Figure 1:
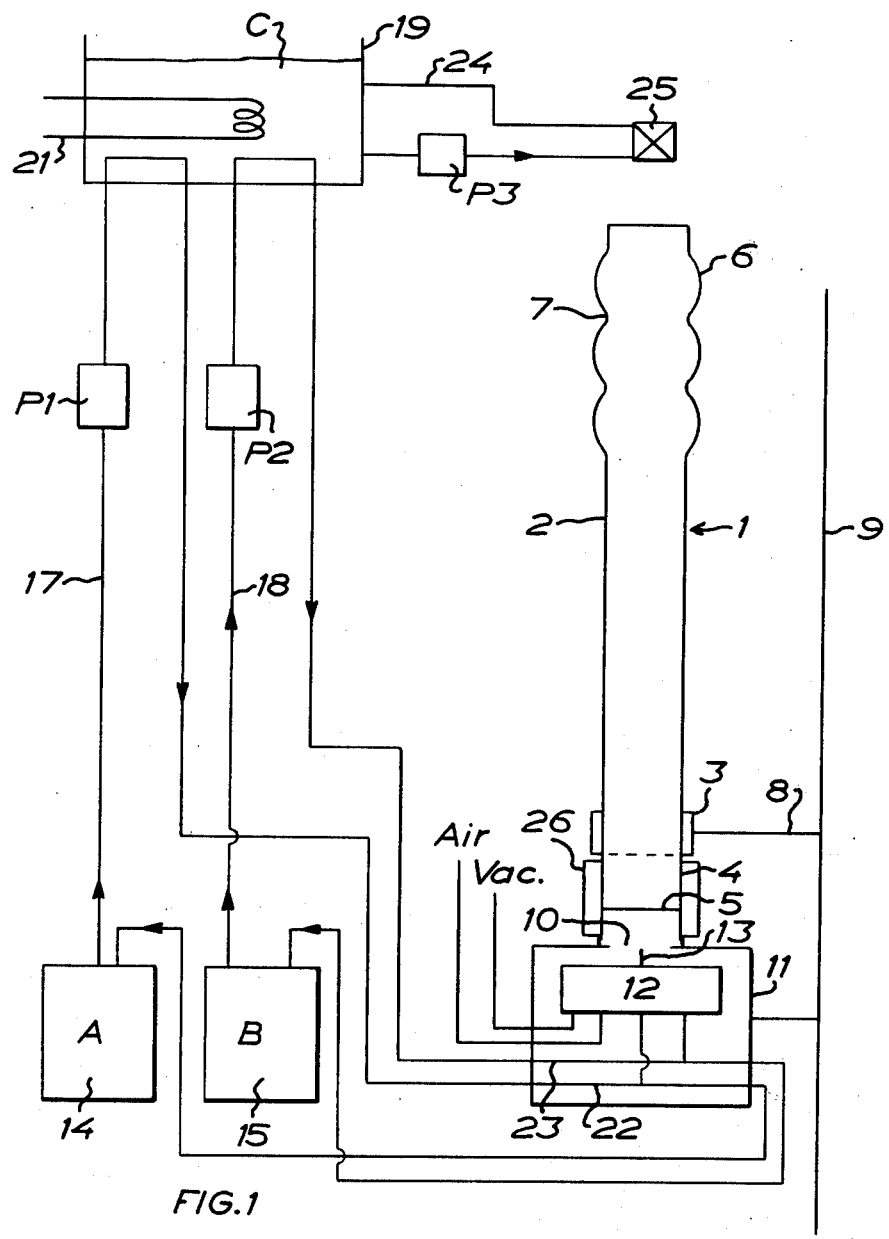

United States Patent [19]

Rynde et al.

[11] 4,184,961
[45] Jan. 22, 1980

[54] EXTRACTION APPARATUS, PREFERABLY FOR ANALYZING PURPOSES

[75] Inventors: Leif G. R. Rynde, Skyttorp; Carl P. Nordbeck, Karlskrona, both of Sweden

[73] Assignee: Tecator Instrument AB, Hoganas, Sweden

[21] Appl. No.: 877,959

[22] Filed: Feb. 15, 1978

[51] Int. Cl.² ............................................. B01D 29/20
[52] U.S. Cl. .................................. 210/232; 210/249; 210/416 R; 210/424
[58] Field of Search ............... 210/232, 416, 238, 249, 210/455, 510, 424, 183; 23/267 R

[56] References Cited

U.S. PATENT DOCUMENTS

| | | | |
|---|---|---|---|
| 2,436,077 | 2/1948 | Robertson | 210/416 |
| 2,612,036 | 9/1952 | Anpang | 210/416 |
| 2,649,205 | 8/1955 | Quinn | 210/416 |
| 3,257,170 | 6/1966 | Marcus et al. | 210/416 |
| 3,356,218 | 12/1967 | Grudoski | 210/416 |
| 3,565,256 | 2/1971 | Loeffler | 210/416 |
| 3,791,524 | 2/1974 | Cho | 210/232 |
| 3,831,759 | 8/1974 | Gelman | 210/232 |
| 3,956,130 | 5/1976 | Cunningham et al. | 210/416 |
| 4,006,084 | 2/1977 | Priest | 210/183 |
| 4,055,498 | 10/1977 | Radnoti | 210/232 |

*Primary Examiner*—Theodore A. Granger
*Attorney, Agent, or Firm*—Buckham and Archer

[57] ABSTRACT

An extraction apparatus for extraction analysis of solid material is described, which consists of an extraction column mounted on a frame and a tubular filter holder mounted on the frame beneath the column. The holder is movable in the frame into and out of engagement with the lower end of the column.

A multi-port valve is connectable to the lower end of the holder for supply of extraction liquid and flushing liquid to the column through the filter and for withdrawal of extraction liquid and flushing liquid from the column through the filter. The filter holder is removable from the frame for analysis of the solid material remaining after the extraction.

5 Claims, 2 Drawing Figures

EXTRACTION APPARATUS, PREFERABLY FOR ANALYZING PURPOSES

This invention relates to an extraction apparatus for treating, preferably analyzing solid material, comprising a tube with an open upper end for supply of fluid and a lower end equipped with a filter.

Most of the prior art extraction apparatuses comprise a column with a filter at the lower end thereof. A problem encountered in such prior art apparatuses is that the filter may be clogged during extraction and after extraction when the extracting agent is drawn off the column through the filter, which prevents an overall contact between the material being extracted and the extracting agent or a sufficiently rapid draw-off of the extracting agent. Moreover, the construction of the prior art columns is such as to prevent a rapid and effective introduction into the column of the material to be extracted and the extraction residues to be subjected to further extraction steps, and withdrawal from the column of extraction residues having been subjected to extraction steps.

The object of the present invention is to find a solution to these problems.

To this end, the filter at the lower end of the tube is a filter body disposed in a filter holder, the tube and filter holder are arranged in a frame and engageable with and disengageable from one another at the lower end of the tube by a substantially linear relative vertical movement of them in the frame, and the lower end of the filter holder is connected to feed means for drawing off fluid through the filter and/or introducing fluid from below through the filter.

Figure 2:
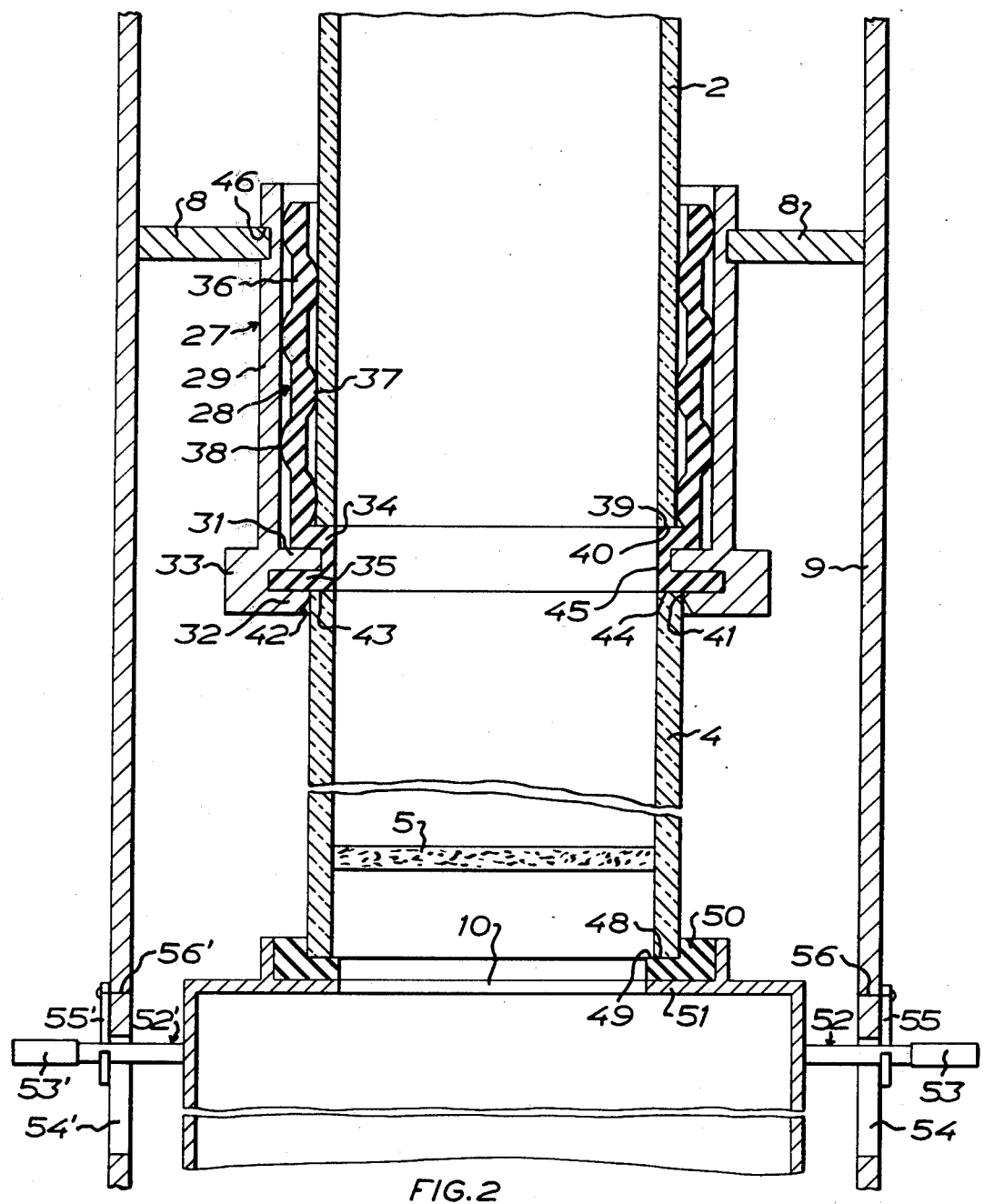

The invention is described in greater detail hereinbelow with reference to the accompanying drawings in which FIG. 1 is a schematic elevation of an extraction analysis apparatus according to the invention, inserted in an extraction system from which part of a frame has been removed;

FIG. 2 is a section of parts of the extraction apparatus shown in FIG. 1.

The apparatus shown in FIG. 1 comprises an extraction column 1 consisting of a vertically disposed tube 2 of circular section, e.g. of glass, and a holder 4 in the form of a tube of circular section, e.g. of glass, for a filter 5, said holder being sealed in relation to the tube 2 but releasably connected thereto by means of a connection piece 3 to be described in the following. The upper part of the tube 2 in alternating succession has ball-shaped enlargements 6 and straight constrictions 7, and the tube is retained by a holder 8 which is secured to the connection piece and to a frame 9. The filter 5 consists of e.g. sintered glass and is fixed in the holder 4, e.g. by fusion. The filter holder 4 is sealingly, but releasably connected at the lower end to an opening 10 of a housing 11 for a five-port four-way valve 12, one port 13 of which is sealingly connected to said opening 10 in a manner not shown in detail. The other valve ports are connectable to said one port 13 in any previously known manner, for instance by displacement or rotation of a slide, and are themselves connected via couplings (not shown) on the valve housing to containers 14, 15 for extracting agent A and B, respectively, compressed air and vacuum. The valve housing is supported in the frame 9 by a mechanism to be described hereinbelow adapted to bring the filter holder into releasable sealing engagement with the tube 2.

In most extraction processes it is desired to supply the extracting agents to the column in a condition heated to a predetermined temperature. To satisfy this desire the conduits 17, 18 for supplying the extracting agent A and B, respectively, to the valve 12 are each connected to a pump P1, P2 and pass through a liquid receptacle 19 containing a thermostat-controlled resistance wire loop 21 and further through the valve housing back to the containers 14, 15. Those parts 22, 23 of the conduits 17, 18 which extend through the valve housing 11 and to which the valve inlet ports for extracting agents A, B are connected, can thus heat the valve, which contributes to maintaining the desired preheating temperature, set by the thermostat, of the extracting agents when they are supplied to the column 1. The liquid C in the receptacle 19 is passed by means of a conduit 24 and a pump P3 through a manual shut-off valve 25 back to the receptacle 19. The valve 25 is disposed directly above the top of the column and can be opened for drawing liquid C from the receptacle 19 to the column 1. Heating means 26, for instance an IR-heater, can be arranged round the filter holder 4 for maintaining the desired temperature in the column.

FIG. 2 shows a section of the connection piece, part of the filter holder, the tube, the valve housing and the frame with the aforementioned mechanism for bringing the filter holder into releasable sealing engagement with the tube 2; the heating means is removed. The connection piece consists of a tubular sleeve 27, e.g. of steel, and a tubular elastic sealing element 28, for instance of rubber, disposed in said sleeve 27. The sleeve has a body portion 29 of substantially uniform thickness, said body portion having at the lower end two spaced apart, inwardly extending annular flanges 31 and 32 and an outwardly projecting annular reinforcing flange 33. The upper flange 31 is grasped with interference fit by parts 34, 35 of a flange which projects inwardly from the body portion of the sealing element, the lower flange portion 35 of the sealing element engaging with interference fit in the space between the two flanges of the sleeve. The body portion 36 of the sealing element extends in an upward direction from the radially outer end of the upper flange portion 34 and in alternating succession has inwardly and outwardly extending, substantially semi-circular annular beads 37 and 38, respectively, which by reason of the insertion of the tube into the sealing element are slightly deformed and thus sealingly engage with the outer side of the tube 2 and the inner side of the sleeve 27. The tube 2 is so inserted in the sealing element 28 that the lower edge surface 39 of the tube sealingly engages the upper surface 40 of the upper flange portion 34 of the sealing element, the inner beads 37 snugly maintaining the tube in this inserted position. By reason of the arrangement of alternating inner and outer beads a uniform load in obtained on the outer side of the tube, the inner side of the sleeve and on the sealing element. The inwardly facing surface of the lower sleeve flange 32 has a straight vertical portion 41 which surrounds the upper end of the filter holder with slide fit, and a portion 42 which widens from said vertical portion 41 towards the underside of the flange. The upper edge surface 43 of the filter holder is pressed into sealing engagement with a part 44 of the lower surface of the lower flange portion 35 of the sealing element, said part 44 being devoid of a flange 32. The radially inner vertical surface 45 of the sealing element which connects the upper surface 40 of the upper flange portion 34 of the sealing element and the lower free surface portion 44 of the lower flange portion 35 of the sealing element is altogether smooth and its diameter is equal to the inner diameters of the tube and the filter holder, that is to say, said vertical surface 45 is aligned with the inner sides of the tube 2 and the filter holder 4 so that a smooth transition is obtained between the inner sides of the tube and the filter holder. The sleeve 27 has a peripheral groove 46 for firm engagement with the holder 8. The surface 48 of the lower edge of the filter holder is sealingly supported on a shoulder 49 of an annular elastic packing 50, e.g. of rubber, which is supported by a flange 51 of the valve housing 11, which extends into said opening 10 of said valve housing.

Rods 52, 52' fixed to the valve housing 11 extend outwards through vertical slots 54, 54' in the frame 9 and at the outer ends have handles 53, 53'. By means of hooks 55, 55', pivotally mounted on axes 56, 56' secured in the frame 9, said rods 52, 52' can be latched so that sealing engagement is established between the surface 43 of the upper edge of the filter holder and the free undersurface 44 of the lower sealing element flange portion as well as between the surface 48 of the lower edge of the filter holder and the shoulder 49 of the packing 50. For release of said sealing engagement the hooks 55, 55' are swung out of engagement with the rods 52, 52' whereupon said rods are moved downwards in the slots 54, 54' by means of handles 53, 53'. By the sliding engagement between the upper portion of the filter holder and the surface 41 of the sleeve flange the filter holder supported by the valve housing takes part in the vertical downward movement of the valve housing, the lower ends of the slots 54, 54' occupying such a position that when the handles 53, 53' are in said lower ends the filter holder is free from the connection piece. To establish renewed sealing engagement between the connection piece and the filter holder the rods are moved upwards to the upper ends of the slots and are latched by means of the hooks 55, 55'. The insertion of the filter holder in the connection piece is facilitated by the guide surface 42 of the lower sleeve flange 32. As the pressure from the filter holder against the sealing element is substantially taken up by the upper flange of the sleeve which is secured to the frame, the upper flange portion 34 of the sealing element is not essentially actuated by said pressure so that the upper side 40 of said flange portion is retained in sealing engagement with the surface 39 of the lower edge of the tube and no folds are formed on the surface 45, i.e. it remains smooth and aligned with the inner sides of the tube 2 and the filter holder 4. It should be noted that the mechanism for raising the filter holder into sealing engagement with the connection piece and the valve opening 10 as well as for release of the filter holder from the connection piece naturally can be of a type other than that illustrated, e.g. a screw, gear, cam or lever arrangement.

For analyzing a comminuted sample of solid material by extraction of the sample with extracting agents A and B and for quantitatively determining the extracts by weighing of the extraction residues, a given amount of the sample is introduced into a filter holder 4 which is placed in the opening 10 of the valve housing in such a way that the surface of the lower edge of the holder rests on the shoulder 49 of the packing 50, whereupon the handles 53, 53' of the rods 52, 52' are grasped and the valve housing with the filter holder 4 is moved upwardly until the rods 52, 52' reach the upper ends of the vertical slots 54, 54', whereby the upper and lower edge surfaces of the filter holder are sealingly engaged with the free undersurface 44 of the lower flange portion of the sealing element and the shoulder 49 of the packing 50, respectively. The container 10 is filled with a liquid C which is indifferent to the sample. A definite quantity of extraction liquid A is supplied to the column from below by corresponding setting of the valve 12, whereupon the valve 12 is adjusted for supply of compressed air to the column. By supply of the extraction liquid A from below via the filter 5 to the column 1 the sample rises up the column from the filter and after supply of compressed air the sample is kept suspended in the column while being agitated by the bubbles of compressed air. After the extraction liquid A has been allowed to act for the desired long time the valve 12 is adjusted for vacuum draw-off from the column of the extracting agent A and the extract dissolved out of the sample. The vacuum is preferably adjustable so that it is low at the start of the draw-off operation and can be increased according as the weight of the liquid column on the filter diminishes, for the purpose of having a uniform draw-off rate. During draw-off the valve 12 is periodically adjusted for supply of compressed air to the column, whereby compressed air raises the solid extraction rest from the filter and prevents said filter from being clogged.

After draw-off of the extracting agent and the extract the extraction residue is washed in the column by opening of the valve 25 and supply of liquid C to the column through the upper end thereof.

As the tube is formed with ball-shaped enlargements and constrictions the liquid will flow uniformly and evenly over the entire inner wall of the tube so that after draw-off of the extracting agent A the solid extraction residues adhering to the tube walls are flushed downwardly towards the filter holder. Because of the smooth transition between the tube and the filter holder the solid material entrained by the washing liquid will not get stuck in the joint between the tube and the filter holder but will be flushed down thereinto. The valve housing is then lowered by means of the handles 53, 53'. During this movement the filter holder which is supported by the valve housing will slide out of the connection piece. Extraction residues can now be dried and weighed for determining the weight thereof and thus the weight of the solid sample constituents which have been extracted by extracting agent A.

After weighing the filter holder with the extraction residues remaining after extraction with extraction liquid A is again inserted in the opening of the valve housing, and the valve housing together with the filter holder is moved by means of the handles 53, 53' into sealing engagement with the connection piece. Extraction liquid B is supplied to the column from below via the filter by corresponding setting of the valve 12, liquid B rising the sample substances up the column from the filter, said substances being kept agitated in extraction liquid B in that the valve 12 is adjusted for admission of compressed air to the column. After extraction liquid B has been sucked off and washed with liquid C in the above-described manner the filter holder is released from the connection piece by loosening of the hooks 55, 55' and lowering of the valve housing by means of the handles 53, 53', and weighed for determination of the sample constituents extracted by means of extracting agent B.

Compressed air need not always be employed, in any case not for purposes of agitation. When extraction is realized for instance under boiling the boiling process can provide sufficient agitation of the sample and the extraction residues in the extraction liquids.

As an example of an analysis associated with extractions and weighing operations, which can be realized by means of the apparatus according to the present invention, mention may be made of plant fiber analysis using e.g. the Weende and Van Soest technique.

The assembly of tube, connecting piece, filter holder and a valve housing which is lowerable and raisable together with the filter holder can of course be utilized in a manner other than that described. Thus all or some of the extraction liquids can be supplied to the column through the upper end thereof. Furthermore, the analysis can be made, not on the solid sample constituents collected in the filter holder, but on the drawn-off and collected extracting agents containing dissolved-out extract, or on both. Several valves can be series-connected in a single valve housing and associated with their respective columns.

What we claim and desire to secure by Letters Patent is:

1. An apparatus for the extraction of a sample of solid material with a liquid which comprises two tubes one detachably superimposed to the other, the upper tube having the upper end open, a filter placed in the lower tube at a distance from its upper end, which filter serves as a container for said solid material, a frame for mounting the two tubes, means for tightly engaging the tubes together and for releasing the tubes by a substantially linear vertical motion, said means being located at the lower end of the upper tube, a multi-port valve detachably connected to the lower end of the lower tube to selectively introduce at least one liquid, compressed gas and vacuum from below the filter, whereby the compressed gas during the extraction stage pushes the sample of solid material upwardly into the upper tube, and wherein the lower end of the upper tube includes an elastic sleeve-shaped element which sealingly surrounds the lower portion of said upper tube and has a radially inwardly directed flange, the upper surface of which engages the lower edge of the tube and the lower surface of which engages the upper edge of the holder lower tube, and the flange of the sleeve-shaped element is provided with an outer annular groove in which is inserted an annular support means for taking up pressure forces against the flange of the elastic element.

2. An apparatus as claimed in claim 1, wherein the support means forms a radially inwardly directed flange of an outer sleeve which surrounds the elastic sleeve-shaped element.

3. An apparatus as claimed in claim 2, wherein the outer sleeve has a further radially inwardly directed flange which forms a guide for the lower tube when the upper edge of the lower tube is brought into engagement with the lower surface of the flange of the elastic element.

4. An apparatus as claimed in claim 3 wherein the inner diameters of the lower tube, the upper tube and the flange of the elastic sleeve-shaped element are of equal size.

5. An apparatus as claimed in claim 4 wherein the multi-port valve has a housing, the lower edge of the lower tube is supported on an elastic packing in an opening provided on said housing, and the apparatus comprises means for moving the valve housing in the direction of the axis of the upper tube and for latching it in the position to which it has been moved.

* * * * *